(12) United States Patent
Oh et al.

(10) Patent No.: US 7,759,079 B2
(45) Date of Patent: Jul. 20, 2010

(54) METHODS OF DIAGNOSING INFLAMMATORY BOWEL DISEASE

(75) Inventors: Esther H. Oh, San Diego, CA (US); John F. Marcelletti, San Diego, CA (US); Susan M. Carroll, San Diego, CA (US); Katie M. Smith, Carlsbad, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 207 days.

(21) Appl. No.: 11/128,011

(22) Filed: May 11, 2005

(65) Prior Publication Data

US 2006/0003392 A1 Jan. 5, 2006

Related U.S. Application Data

(60) Provisional application No. 60/571,216, filed on May 13, 2004.

(51) Int. Cl.
*G01N 33/53* (2006.01)
(52) U.S. Cl. .................. 435/7.31; 435/7.32; 435/7.1; 435/7.2
(58) Field of Classification Search .................. None
See application file for complete search history.

(56) References Cited

U.S. PATENT DOCUMENTS

| | | | |
|---|---|---|---|
| 5,750,355 A * | 5/1998 | Targan et al. | 435/7.24 |
| 5,830,675 A * | 11/1998 | Targan et al. | 435/7.24 |
| 5,916,748 A | 6/1999 | Targan et al. | |
| 5,932,429 A | 8/1999 | Targan et al. | |
| 6,033,864 A | 3/2000 | Braun et al. | |
| 6,074,835 A | 6/2000 | Braun et al. | |
| 6,183,951 B1 * | 2/2001 | Plevy et al. | 435/6 |
| 6,218,129 B1 * | 4/2001 | Walsh et al. | 435/7.21 |
| 6,309,643 B1 | 10/2001 | Braun et al. | |
| 6,514,770 B1 * | 2/2003 | Sorin | 436/518 |

(Continued)

FOREIGN PATENT DOCUMENTS

WO   WO 98/37415   8/1998

(Continued)

OTHER PUBLICATIONS

Walker, LJ et al, Clin. Exp. Immunol, 2004, vol. 135, pp. 490-496, Anti-Saccharomyces cerevisiae antibodies (ASCA) in Crohn's disease are associated with disease severity but not NOD2/CARD15 mutations.*

(Continued)

*Primary Examiner*—Robert B Mondesi
*Assistant Examiner*—Ginny Portner
(74) *Attorney, Agent, or Firm*—Townsend and Townsend and Crew LLP

(57) ABSTRACT

The present invention provides methods for diagnosing the presence or severity of inflammatory bowel disease (IBD) in an individual and methods for stratifying IBD by determining the level of one or more IBD markers in a sample from the individual and calculating an index value using an algorithm based upon the level of the IBD markers. Methods for monitoring the efficacy of IBD therapy, monitoring the progression or regression of IBD, and optimizing therapy in an individual having IBD are also provided.

21 Claims, 1 Drawing Sheet

U.S. PATENT DOCUMENTS

| | | | |
|---|---|---|---|
| 6,627,458 B2 * | 9/2003 | Worman et al. | 436/507 |
| 2003/0003518 A1 * | 1/2003 | Worman et al. | 435/7.21 |
| 2004/0043931 A1 * | 3/2004 | Hersberg et al. | 514/12 |
| 2004/0137536 A1 * | 7/2004 | Boone et al. | 435/7.2 |
| 2006/0154276 A1 * | 7/2006 | Lois et al. | 435/6 |
| 2007/0275424 A1 * | 11/2007 | Gewirtz et al. | 435/7.92 |

FOREIGN PATENT DOCUMENTS

| | | | |
|---|---|---|---|
| WO | 99/60403 | * | 11/1999 |
| WO | 9960403 | * | 11/1999 |
| WO | 01/89361 | * | 11/2001 |
| WO | WO 01/89381 A2 | | 11/2001 |
| WO | 0239883 | * | 5/2002 |
| WO | WO 03/053220 A2 | | 7/2003 |
| WO | 2004/037073 | * | 5/2004 |
| WO | WO 2004/037073 | | 5/2004 |
| WO | 2004/048600 | * | 6/2004 |
| WO | WO 2004/048600 A2 | | 6/2004 |

OTHER PUBLICATIONS

Abstract Only Kuno, Y et al, J. Gastroenterol. Nov. 2002, vol. 37(Suppl 14), pp. 22-32, Possible involvement of neutrophil elastase in imparied mucosal repair in patients with ulcerative colitis. (abstract only).*

Nakamura, Robert M. et al, Clinica Chimica ACTA, vol. 335, Sep. 2003, pp. 9-20, Advances in clinical laboratory tests for inflammatory bowel disease.*

Reumaux, Dominique PhD, Best Practice & Research Clinical Gastroenterology, vol. 17(1), pp. 19-35. 2003, Serological markers in inflammatory bowel diseases.*

Dubinsky, Maria C et al, The American Journal of Gastroenterology, vol. 96(3), 2001, pp. 758-768, Clinical Utility of Serodiagnostic testing in suspected pediatric Inflammatory Bowel Disease.*

Quinton et al, Gut, vol. 42, June , pp. 788-791.*

Vasiliauskas, Ea et al, Gut 200, vol. 47, pp. 487-496, Marker Antibody expression stratifies Crohn's disease into immunologically homogeneous subgroups with distinct clincal characteristics.*

Nakamura, Robert M et al, Clinica Chimica Acta, vol. 335, 2003, pp. 9-20.*

Berkson 1944 formula named Logit is: $y = \exp(b0 + b1^*x1 + \ldots + bn^*xn)/\{1 + \exp(b0 + b1^*x1 + \ldots + bn^*xn)\}$.*

Reumaux, D, 2003, Best Practice and Research Cinical Gastroenterology, reference of record.*

Quinton, JF et al, Gut, 1988, 42, pp. 788-791, reference of record.*

Sostegni et al, Alimentary Tract, Digest Liver Disease, vol. 33, pp. 755-761, 2001, Detection of anti-Saccharomyces cerevisiae antibodies in Crohn's disease: is it a reliable diagnostic and prognostic marker?*

Lombardi, Giovanni et al, Dis. Colon Rectum, 2000, vol. 43, pp. 999-1007, Antineutrophil cytoplasmic antibodies in Inflammatory Bowel Disease.*

Arnott, et al., Sero-Reactivity to Microbial Components in Crohn's Disease is Associated with Disease Severity and Progression, but not NOD2/CARD15 Genotype; American Journal of Gastroenterology; 2004; 99:2376-2384; Blackwell Publishing.

Nakamura, R.M. et al. "Advances in clinical laboratory tests for Inflammatory bowel disease." *Clinica Chimica Acta* (2003). vol. 335, pp. 9-20.

U.S. Appl. No. 11/565,544, filed Nov. 30, 2006, Augusto Lois, et al.

* cited by examiner

//METHODS OF DIAGNOSING INFLAMMATORY BOWEL DISEASE

CROSS-REFERENCES TO RELATED APPLICATIONS

The present application claims priority to U.S. Provisional Application No. 60/571,216, filed May 13, 2004, which is herein incorporated by reference in its entirety for all purposes.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases. The cost of IBD and IBS is compounded by lost productivity, with people suffering from these disorders missing at least 8 more days of work annually than the national average.

Inflammatory bowel disease has many symptoms in common with irritable bowel syndrome, including abdominal pain, chronic diarrhea, weight loss, and cramping, making definitive diagnosis extremely difficult. Of the 5 million people suspected of suffering from IBD in the United States, only 1 million are diagnosed as having IBD. The difficulty in differentially diagnosing IBD and IBS hampers early and effective treatment of these diseases. Thus, there is a need for rapid and sensitive testing methods for definitively distinguishing IBD from IBS.

Although progress has been made in precisely diagnosing clinical subtypes of IBD, current methods for diagnosing an individual as having either Crohn's disease, ulcerative colitis, or indeterminate colitis are relatively costly and require labor-intensive clinical, radiographic, endoscopic, and/or histological techniques. These costly techniques may be justified for those individuals previously diagnosed with or strongly suggested to have IBD, but a less expensive and highly sensitive alternative would be advantageous for first determining if an individual even has IBD. Such a highly sensitive primary screening assay would provide physicians with an inexpensive means for rapidly distinguishing individuals with IBD from those having IBS, thereby facilitating earlier and more appropriate therapeutic intervention and minimizing uncertainty for patients and their families. The primary screening assay could then be combined with a subsequent, highly specific assay for determining if an individual diagnosed with IBD has either Crohn's disease, ulcerative colitis, or indeterminate colitis.

Unfortunately, highly sensitive and inexpensive screening assays for distinguishing IBD from other digestive diseases presenting with similar symptoms and for differentiating between clinical subtypes of IBD are currently not available. Thus, there is a need for improved methods of diagnosing IBD at a very early stage of disease progression and for stratifying IBD into a clinical subtype such as Crohn's disease, ulcerative colitis, or indeterminate colitis. The present invention satisfies these needs and provides related advantages as well.

BRIEF SUMMARY OF THE INVENTION

The present invention provides methods for diagnosing the presence or severity of inflammatory bowel disease (IBD) in an individual by determining the level of one or more IBD markers in a sample from the individual and calculating an index value using an algorithm based upon the level of the IBD markers. The present invention also provides methods for stratifying IBD by differentiating between Crohn's disease (CD), ulcerative colitis (UC), and indeterminate colitis (IC) in an individual by determining the level of one or more IBD markers in a sample from the individual and calculating an index value using an algorithm based upon the level of the IBD markers. In addition, the present invention provides methods for monitoring the efficacy of IBD therapy, monitoring the progression or regression of IBD, and optimizing therapy in an individual having IBD by determining the level of one or more IBD markers in a sample from the individual and calculating an index value using an algorithm based upon the level of the IBD markers.

In one aspect, the present invention provides a method for diagnosing the presence or severity of IBD in an individual, the method comprising:

(a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;

(b) calculating an index value for the individual using an algorithm based upon the level of at least one marker; and (c) diagnosing the presence or severity of IBD in the individual based upon the index value.

In certain instances, when an individual is diagnosed as having IBD based upon the index value, the methods of the present invention can further comprise diagnosing the clinical subtype of IBD in the individual. For example, the individual can be diagnosed as having a clinical subtype of IBD such as CD, UC, or IC.

In another aspect, the present invention provides a method for differentiating between CD, UC, and IC in an individual, the method comprising:

(a) determining a level of at least one marker selected from the group consisting of ANCA, ASCA-IgA, ASCA-IgG, an anti-OmpC antibody, an anti-I2 antibody, and an anti-flagellin antibody in a sample from the individual;

(b) calculating an index value for the individual using an algorithm based upon the level of at least one marker; and (c) diagnosing the individual as having CD, UC, or IC based upon the index value.

In yet another aspect, the present invention provides a method for monitoring the efficacy of IBD therapy in an individual, the method comprising:

(a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;

(b) calculating an index value for the individual using an algorithm based upon the level of at least one marker; and (c) determining the presence or severity of IBD in the individual based upon the index value.

Instill yet another aspect, the present invention provides a method for monitoring the progression or regression of IBD in an individual, the method comprising:

(a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;

(b) calculating an index value for the individual using an algorithm based upon the level of at least one marker; and (c) determining the presence or severity of IBD in the individual based upon the index value.

In a further aspect, the present invention provides a method for optimizing therapy in an individual having IBD, the method comprising:

(a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;

(b) calculating an index value for the individual using an algorithm based upon the level of at least one marker; and (c) determining a course of therapy in the individual based upon the index value.

Other objects, features, and advantages of the present invention will be apparent to one of skill in the art from the following detailed description and FIGURE.

DETAILED DESCRIPTION OF THE INVENTION

I. Definitions

Figure 1:
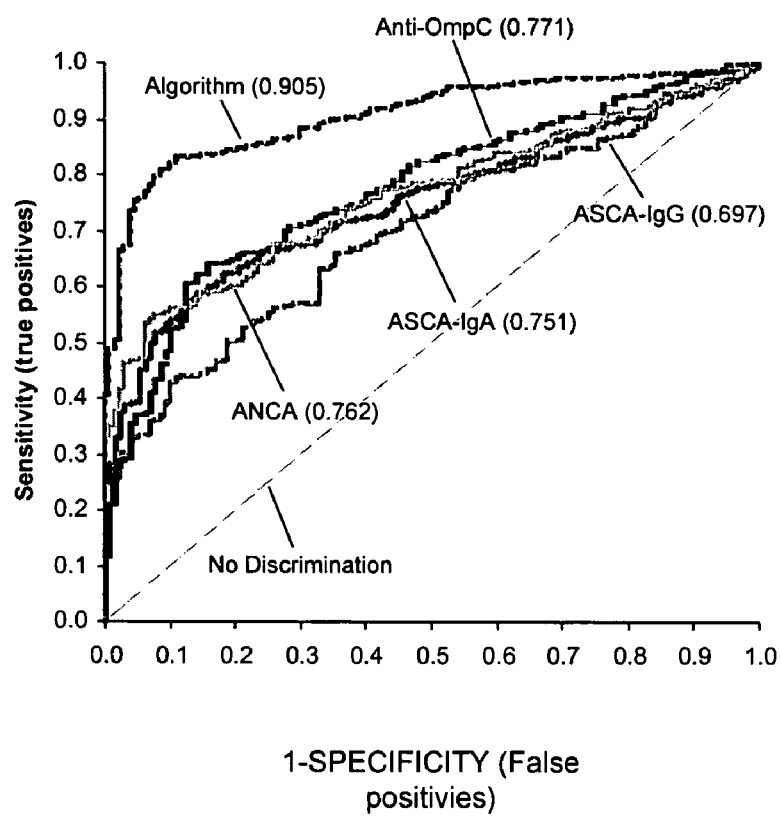
FIG. 1 shows a graph comparing the sensitivity and specificity of diagnosing IBD using an algorithm of the present invention versus using the level of individual IBD markers. The values in parentheses represent the area under the curve (AUC).

As used herein, the following terms have the meanings ascribed to them unless specified otherwise.

The term "inflammatory bowel disease" or "IBD" refers to gastrointestinal disorders including, without limitation, Crohn's disease (CD), ulcerative colitis (UC), and indeterminate colitis (IC). Inflammatory bowel diseases such as CD, UC, and IC are distinguished from all other disorders, syndromes, and abnormalities of the gastroenterological tract, including irritable bowel syndrome (IBS).

The term "sample" refers to any biological specimen obtained from an individual that contains antibodies. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-86 (1997)). One skilled in the art understands that samples such as serum samples can be diluted prior to the analysis of marker levels.

The term "IBD marker" refers to any biochemical marker, serological marker, genetic markers, or other clinical or echographic characteristic that can be used in diagnosing IBD or a clinical subtype of thereof such as CD, UC, or IC. Examples of biochemical and serological markers include, without limitation, anti-neutrophil cytoplasmic antibodies (ANCA), anti-*Saccharomyces cerevisiae* immunoglobulin A (ASCA-IgA), anti-*Saccharomyces cerevisiae* immunoglobulin G (ASCA-IgG), anti-outer membrane protein C (anti-OmpC) antibodies, anti-I2 antibodies, anti-flagellin antibodies, elastase, lactoferrin, calprotectin, and combinations thereof. An example of a genetic marker is the NOD2/CARD15 gene.

The term "clinical factor" refers to a symptom in an individual that is associated with IBD. Suitable clinical factors include, without limitation, diarrhea, abdominal pain, cramping, fever, anemia, weight loss, anxiety, depression, and combinations thereof. In one embodiment, a diagnosis of IBD is based upon a combination of comparing an index value for an individual to a threshold value and determining whether the individual has one or more clinical factors.

The term "algorithm" refers to any of a variety of statistical analyses used to determine relationships between variables. In the present invention, the variables are levels of IBD markers and the algorithm is used to determine, e.g., whether an individual has IBD or whether an individual has CD, UC, or IC. In one embodiment, logistic regression is used. In another embodiment, linear regression is used. Other statistical methods known to those of skill in the art are also suitable for use in the present invention and include, without limitation, artificial neural networks (ANN), neuro fuzzy networks (NFN), multilayer perceptron (MLP), and learning vector quantization (LVQ) (Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); Hassoun, "Fundamentals of Artificial Neural Networks," MIT Press, Cambridge, Mass., London (1995)). Another useful statistical method called Classification and Regression Trees (CART) can be used in the present invention (see, Breiman et al. Classification and Regression Trees, Chapman and Hall, New York (1984)). Any number of IBD markers can be analyzed using an algorithm according to the methods of the present invention. For example, levels of 1, 2, 3, 4, 5, 6, 7, 8, 9, 10, 15, 20, 25, 30, 35, 40, 50, or more IBD markers can be included in an algorithm. In a preferred embodiment, levels of at least one of six IBD markers, i.e., ANCA, ASCA-IgA, ASCA-IgG, anti-OmpC antibodies, anti-I2 antibodies, and anti-flagellin antibodies, are determined and analyzed using logistic regression to diagnose an individual as having IBD or to diagnose an individual as having a clinical subtype of IBD. In another preferred embodiment, the algorithm has the following formula:

Index Value=$\text{Exp}(b_0+b_1*x_1+\ldots+b_n*x_n)/(1+\text{Exp}(b_0+b_1*x_1+\ldots+b_n*x_n))$, wherein
 $b_0$ is an intercept value;
 $b_1$ is the regression coefficient of the first marker;
 $x_1$ is the concentration level of the first marker;
 $b_n$ is the regression coefficient of the $n^{th}$ marker; and
 $x_n$ is the concentration level of the $n^{th}$ marker.

For example, when all six of the above IBD markers are determined and analyzed using the above algorithm, n is 6. However, one skilled in the art will appreciate that additional markers including, but not limited to, elastase, lactoferrin, and calprotectin can also be determined and analyzed using the above algorithm such that n is an integer greater than 6.

The term "index value" refers to a number for an individual that is determined using an algorithm for diagnosing IBD or a clinical subtype thereof. In a preferred embodiment, the index value is determined using logistic regression and is a number between 0 and 1.

The term "threshold value" or "index cutoff value" refers to a number chosen on the basis of population analysis that is used for comparison to an index value of an individual and for diagnosing IBD or a clinical subtype thereof. Thus, the threshold value is based on analysis of index values determined using an algorithm. Those of skill in the art will recognize that a threshold value can be determined according to the needs of the user and characteristics of the analyzed population. When the algorithm is logistic regression, the threshold value will, of necessity, be between 0 and 1. Ranges for threshold values include, e.g., 0.1 to 0.9, 0.2 to 0.8, 0.3 to 0.7, and 0.4 to 0.6. Once a threshold value is determined, it is compared to an index value for an individual. A disease state can be indicated by an index value above or below the threshold value. In a preferred embodiment, the index value is calculated using the algorithm of the above formula and an individual is diagnosed as having IBD when the index value is greater than the threshold value. In this embodiment, an individual is diagnosed as not having IBD when the index value is less than the threshold value. In another embodiment, the index value is calculated using the algorithm of the above formula and an individual is diagnosed as having CD when the index value is greater than the threshold value. In an alternative embodiment, an individual is diagnosed as having UC when the index value is greater than the threshold value. In another alternative embodiment, an individual is diagnosed as having IC when the index value is greater than the threshold value.

In certain other aspects, the algorithms of the present invention can use a quantile measurement of a particular marker within a given population as a variable. Quantiles are a set of 'cut points' that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations.

The present invention can include the use of percentile ranges of marker levels (e.g. tertiles, quartile, quintiles), or their cumulative indices (e.g. quartile sums of marker levels) as variables in the algorithms (just as with continuous variables).

The term "iterative approach" refers to the analysis of IBD markers from an individual using more than one algorithm and/or threshold value. For example, two or more algorithms could be used to analyze different sets of IBD markers. As another example, a single algorithm could be used to analyze IBD markers, but more than one threshold value based on the algorithm could be used for diagnosis. In a preferred embodiment, iterative approach refers to the analysis of IBD markers using the algorithm of the above formula to calculate a first index value that is compared to a first threshold value to diagnose IBD, and using the algorithm of the above formula to calculate a second index value that is compared to a second threshold value to diagnose CD, UC, or IC.

The term "prognosis" refers to a prediction of the probable course and outcome of IBD or the likelihood of recovery from IBD. In one embodiment, the index value is indicative of a prognosis of IBD in an individual. For example, the prognosis can be surgery, development of one or more clinical factors, development of intestinal cancer, or recovery from the disease.

The term "diagnosing the presence or severity of IBD" refers to methods for determining the presence or absence of IBD in an individual. The term also refers to methods for assessing the level of disease activity in an individual. The severity of IBD can be evaluated using any of a number of methods known to one skilled in the art. In some embodiments, the methods of the present invention are used to diagnose a mild, moderate, severe, or fulminant form of IBD based upon the criteria developed by Truelove et al., *Br. Med. J.*, 12:1041-1048 (1955) for assessing disease activity in ulcerative colitis. For example, an individual having less than or equal to 5 daily bowel movements, small amounts of hematochezia, a temperature of less than 37.5° C., a pulse of less than 90/min, an erythrocyte sedimentation rate of less than 30 mm/hr, and a level of hemoglobin greater than 10 g/dl can be diagnosed as having a mild form of IBD. An individual having greater than 5 daily bowel movements, large amounts of hematochezia, a temperature of greater than or equal to 37.5° C., a pulse of greater than or equal to 90/min, an erythrocyte sedimentation rate of greater than or equal to 30 mm/hr, and a level of hemoglobin less than or equal to 10 g/dl can be diagnosed as having a severe form of IBD. An individual with fewer than all six of the critera for severe IBD has a moderate form of IBD. An individual having more than 10 bowel movements per day, continuous bleeding, abdominal distention and tenderness, and radiologic evidence of edema and possibly bowel dilation can be diagnosed as having a fulminant form of IBD. In other embodiments, the methods of the present invention are used to diagnose a mild to moderate, moderate to severe, or severe to fulminant form of IBD based upon the criteria developed by Hanauer et al., *Am. J. Gastroenterol.*, 92:559-566 (1997) for assessing disease activity in Crohn's disease. For example, an individual able to tolerate oral intake without dehydration, high fevers, abdominal pain, abdominal mass, or obstruction can be diagnosed as having mild to moderate IBD. An individual who has failed to respond to therapy for mild to moderate disease or who has a fever, weight loss, abdominal pain, anemia, or nausea/vomiting without frank obstruction can be diagnosed as having moderate to severe IBD. An individual with persisting symptoms despite the introduction of steroids on an outpatient basis or who has a high fever, persistent vomiting, obstruction, rebound tenderness, cachexia, or an abscess can be diagnosed as having severe to fulminant IBD. In certain instances, index cutoff values are determined for each level of disease activity and the index value is compared to one or more of these index cutoff values. In certain other instances, index cutoff values are determined for a combination of disease activity levels (e.g., mild and moderate or severe and fulminant) and the index value is compared to one or more of these index cutoff values.

The term "monitoring the progression or regression of IBD" refers to the use of the algorithms of the present invention to determine the disease state (e.g., severity of IBD) of an individual. In one embodiment, the index value of the individual is compared to an index value for the same individual that was determined at an earlier time. In certain instances, the algorithms of the present invention can also be used to predict the progression of IBD, e.g., by determining a likelihood for IBD to progress either rapidly or slowly in an individual based on the levels of markers in a sample. In certain other instances, the algorithms of the present invention can also be used to predict the regression of IBD, e.g., by determining a likelihood for IBD to regress either rapidly or slowly in an individual based on the levels of markers in a sample.

The term "monitoring the efficacy of IBD therapy" refers to the use of the algorithms of the present invention to determine the disease state (e.g., severity of IBD) of an individual after a therapeutic agent has been administered. In one embodiment, the index value of the individual is compared to an index value for the same individual that was determined before initiation of use of the therapeutic agent or at an earlier time in therapy. As used herein, a therapeutic agent useful in IBD therapy is any compound, drug, procedure, or regimen used to improve the health of an individual and includes, without limitation, aminosalicylates such as mesalazine and sulfasalazine, corticosteroids such as prednisone, thiopurines such as azathioprine and 6-mercaptopurine, methotrexate, monoclonal antibodies such as infliximab, surgery, and a combination thereof.

The term "optimizing therapy in an individual having IBD" refers to the use of the algorithms of the present invention to determine the course of therapy for an individual before a therapeutic agent has been administered or to adjust the course of therapy for an individual after a therapeutic agent has been administered in order to optimize the therapeutic efficacy of the therapeutic agent. In one embodiment, the index value of the individual is compared to an index value for the same individual that was determined at an earlier time during the course of therapy. As such, a comparison of the two index values provides an indication for the need to change the course of therapy or an indication for the need to increase or decrease the dose of the current course of therapy.

The term "course of therapy" refers to any therapeutic approach taken to relieve or prevent one or more symptoms (i.e., clinical factors) associated with IBD. The term encompasses administering any compound, drug, procedure, or regimen useful for improving the health of an individual with IBD and includes any of the therapeutic agents described above. One skilled in the art will appreciate that either the course of therapy or the dose of the current course of therapy can be changed based upon the index values determined using the methods of the present invention.

The term "anti-neutrophil cytoplasmic antibody" or "ANCA" as used herein refers to antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). The term ANCA, as used herein, encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G. ANCA levels in a sample from an individual can be determined, for example, using an immunoassay such as an enzyme-linked immunosorbent assay (ELISA) with alcohol-fixed neutrophils or using an immunohistochemical assay such as an indirect fluorescent antibody (IFA) assay. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, Bacteroides antigens, or ANCA-reactive fragments thereof (see, e.g., U.S. Pat. No. 6,033,864); secretory vesicle antigens or ANCA-reactive fragments thereof (see, e.g., U.S. application Ser. No. 08/804,106); and anti-ANCA idiotypic antibodies. One skilled in the art will appreciate that the use of additional antigens specific for ANCA is within the scope of the present invention.

The term "anti-*Saccharomyces cerevisiae* immunoglobulin A" or "ASCA-IgA" refers to antibodies of the immunoglobulin A isotype that react specifically with *S. cerevisiae*. Similarly, the term "anti-*Saccharomyces cerevisiae* immunoglobulin G" or "ASCA-IgG" refers to antibodies of the immunoglobulin G isotype that react specifically with *S. cerevisiae*. The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Application Publication No. 20030105060, e.g., D-Man β(1-2) D-Man β(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

The term "anti-outer membrane protein C antibody" or "anti-OmpC antibody" refers to antibodies directed to a bacterial outer membrane porin as described in, e.g., PCT Publication No. WO 01/89361. The term "outer membrane protein C" or "OmpC" refers to a bacterial porin that is immunoreactive with an anti-OmpC antibody. The level of anti-OmpC antibody present in a sample from an individual can be determined using an OmpC protein or a fragment thereof such as an immunoreactive fragment thereof. The OmpC antigen can be prepared, e.g., by purification from enteric bacteria such as *E. coli*, by recombinant means, by synthetic means, or using phage display.

The term "anti-I2 antibody" refers to antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The level of anti-I2 antibody present in a sample from an individual can be determined using an I2 protein or a fragment thereof such as an immunoreactive fragment thereof. The I2 antigen can be prepared, e.g., by purification from a microbe, by recombinant means, by synthetic means, or using phage display.

The term "anti-flagellin antibody" refers to antibodies directed to a protein component of bacterial flagella as described in, e.g., PCT Publication No. WO 03/053220 and U.S. Application Publication No. 20040043931. The term "flagellin" refers to a bacterial flagellum protein that is immunoreactive with an anti-flagellin antibody. The level of anti-flagellin antibody present in a sample from an individual can be determined using a flagellin protein or a fragment thereof such as an immunoreactive fragment thereof. Examples of flagellin proteins suitable for use in the present invention include, without limitation, flagellin X, flagellin A, flagellin B, Cbir-1 flagellin, fragments thereof, and combinations thereof. The flagellin antigen can be prepared, e.g., by purification from bacterium such as *Helicobacter Bilis, Helicobacter mustelae, Helicobacter pylori, Butyrivibrio fibrisolvens*, and bacterium found in the cecum, by recombinant means, by synthetic means, or using phage display.

As used herein, the term "substantially the same amino acid sequence" refers to an amino acid sequence that is similar but not identical to the naturally-occurring amino acid sequence. For example, an amino acid sequence, i.e., polypeptide, that has substantially the same amino acid sequence as an I2 protein can have one or more modifications such as amino acid additions, deletions, or substitutions relative to the amino acid sequence of the naturally-occurring I2 protein, provided that the modified polypeptide retains substantially at least one biological activity of I2 such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "administering" as used herein refers to oral administration, administration as a suppository, topical contact, intravenous, intraperitoneal, intramuscular, intralesional, intranasal or subcutaneous administration, or the implantation of a slow-release device, e.g., a mini-osmotic pump, to an individual. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

II. General Overview

The present invention provides methods for diagnosing the presence or severity of IBD in an individual by determining the level of one or more IBD markers in a sample from the individual and calculating an index value using an algorithm based upon the level of the IBD markers. The present invention also provides methods for stratifying IBD by differentiating between CD, UC, and IC in an individual by determining the level of one or more IBD markers in a sample from the individual and calculating an index value using an algorithm based upon the level of the IBD markers. In addition, the present invention provides methods for monitoring the efficacy of IBD therapy, monitoring the progression or regression of IBD, and optimizing therapy in an individual having IBD by determining the level of one or more IBD markers in a sample from the individual and calculating an index value using an algorithm based upon the level of the IBD markers.

The present invention is based upon the surprising discovery that the use of an algorithm based upon the levels of multiple markers for diagnosing IBD is far superior to non-algorithmic techniques for diagnosing IBD that rely on determining the level of only a single IBD marker. By using the methods of the present invention, a diagnosis of IBD is made with substantially greater sensitivity and specificity and the presence of IBD is detected at an earlier stage of disease progression. In addition, the methods of the present invention are capable of differentiating between clinical subtypes of IBD with a high degree of overall accuracy. As a result, the stratification of IBD in a particular individual is achieved in a highly accurate manner.

III. Description of the Embodiments

The present invention provides algorithmic-based methods for diagnosing the presence or severity of IBD and for differentiating between clinical subtypes of IBD such as CD, UC, or IC by determining the level of one or more IBD markers in a sample from an individual. The methods of the present invention are also useful for corroborating an initial diagnosis of IBD or for gauging the progression of IBD in an individual with a previous definitive diagnosis of IBD. In addition, the methods of the present invention are useful for monitoring the status of IBD over a period of time and can further be used to monitor the efficacy of therapeutic treatment.

In one aspect, the present invention provides a method for diagnosing the presence or severity of IBD in an individual, the method comprising:
  (a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;
  (b) calculating an index value for the individual using an algorithm based upon the level of at least one marker; and
  (c) diagnosing the presence or severity of IBD in the individual based upon the index value.

In one embodiment, the index value is compared to an index cutoff value. In a preferred embodiment, the individual is diagnosed as not having IBD when the index value is less than the index cutoff value. In an alternative embodiment, the individual is diagnosed as having a mild or moderate form of IBD when the index value is less than the index cutoff value.

In another preferred embodiment, the individual is diagnosed as having IBD when the index value is greater than the index cutoff value. In an alternative embodiment, the individual is diagnosed as having a severe or fulminant form of IBD when the index value is greater than the index cutoff value. One skilled in the art will appreciate that in certain instances an index value below the index cutoff value can indicate the presence of IBD or a severe or fulminant form of IBD while an index value above the index cutoff value can indicate the absence of IBD or a mild or moderate form of IBD. In some embodiments, the methods of the present invention further comprise sending the index value to a clinician, e.g., a gastroenterologist or a general practitioner.

In another embodiment, the algorithm uses, for example, logistic regression, linear regression, classification trees, or artificial neural networks (ANN). Preferably, the algorithm is a regression algorithm using logistic regression. In certain instances, when the algorithm uses logistic regression, the index value and index cutoff value are between 0 and 1. Suitable ranges for the index cutoff value include, e.g., 0.1 to 0.9, 0.2 to 0.8, 0.3 to 0.7, and 0.4 to 0.6. However, one skilled in the art understands that the index value and index cutoff value can fall within any set of ranges depending on the type of algorithm used.

In yet another embodiment, the index value is calculated based upon the level of at least two, three, four, five, six, or more IBD markers. In a preferred embodiment, the index value is calculated based upon the level of at least two IBD markers. In another preferred embodiment, the index value is calculated based upon the level of ANCA, ASCA-IgA, ASCA-IgG, and anti-OmpC. In still yet another embodiment, the index value is calculated based upon the level of at least one additional IBD marker selected from the group consisting of elastase, lactoferrin, and calprotectin.

In a further embodiment, a diagnosis of IBD is based upon a combination of comparing an index value for an individual to a threshold value and determining whether the individual has at least one clinical factor. A clinical factor refers to a symptom in an individual that is associated with IBD. Suitable clinical factors include, without limitation, diarrhea, abdominal pain, cramping, fever, anemia, weight loss, anxiety, depression, and combinations thereof.

In certain instances, the index value calculated using an algorithm based upon the level of one or more IBD markers is indicative of a prognosis of IBD in the individual. For example, the prognosis can be surgery, development of one or more clinical factors, development of intestinal cancer, or recovery from the disease.

In another embodiment, the sample used for detecting or determining a level of at least one IBD marker is whole blood, plasma, serum, saliva, urine, stool (i.e., feces), tears, and any other bodily fluid, or a tissue sample (i.e., biopsy) such as a small intestine or colon sample. In a preferred embodiment, the sample is serum. In other preferred embodiments, the sample is plasma, urine, feces, or a tissue biopsy. In certain instances, the methods of the present invention further comprise obtaining the sample from the individual prior to detecting or determining a level of at least one IBD marker in the sample.

In yet another embodiment, the index value calculated using an algorithm based upon the level of at least one IBD marker is indicative of a course of therapy for the individual. For example, the index value can be compared to an index cutoff value and a course of therapy can be determined based upon whether the index value is above or below the index cutoff value. In certain instances, the course of therapy is treatment with aminosalicylates such as mesalazine and sulfasalazine, corticosteroids such as prednisone, thiopurines such as azathioprine and 6-mercaptopurine, methotrexate, or monoclonal antibodies such as infliximab. In certain other instances, the course of therapy is surgery. A combination of any of the above courses of therapy is also within the scope of the present invention.

In preferred embodiments of the present invention, the algorithm is a regression algorithm having the following formula:

$$\text{Index Value} = \text{Exp}(b_0 + b_1 * x_1 + \ldots + b_n * x_n) / (1 + \text{Exp}(b_0 + b_1 * x_1 + \ldots + b_n * x_n)),$$

wherein $b_0$ is an intercept value;

$b_1$ is the regression coefficient of the first marker;

$x_1$ is the concentration level of the first marker;

$b_n$ is the regression coefficient of the $n^{th}$ marker;

$x_n$ is the concentration level of the $n^{th}$ marker; and n is an integer of from 1 to 6.

In other preferred embodiments, the level of each IBD marker is determined using an enzyme-linked immunosorbent assay (ELISA). A variety of antigens are suitable for use in detecting and/or determining the level of each IBD marker in an assay such as an ELISA. Antigens specific for ANCA that are suitable for determining ANCA levels include, e.g., fixed neutrophils; unpurified or partially purified neutrophil extracts; purified proteins, protein fragments, or synthetic peptides such as histone H1, histone H1-like antigens, porin antigens, Bacteroides antigens, secretory vesicle antigens, or ANCA-reactive fragments thereof; and combinations thereof. Preferably, the level of ANCA is determined using fixed neutrophils. Antigens specific for ASCA, i.e., ASCA-IgA and/or ASCA-IgG, include, e.g., whole killed yeast cells such as *Saccharomyces* or *Candida* cells; yeast cell wall mannan such as phosphopeptidomannan (PPM); oligosaccharides such as oligomannosides; neoglycolipids; purified antigens; synthetic antigens; and combinations thereof. Antigens specific for anti-OmpC antibodies that are suitable for determining anti-OmpC antibody levels include, e.g., an OmpC protein, an OmpC polypeptide having substantially the same amino acid sequence as the OmpC protein, a fragment thereof such as an immunoreactive fragment thereof, and combinations thereof. Antigens specific for anti-I2 antibodies that are suitable for determining anti-I2 antibody levels include, e.g., an I2 protein, an I2 polypeptide having substantially the same amino acid sequence as the I2 protein, a fragment thereof such as an immunoreactive fragment thereof, and combinations thereof. Antigens specific for anti-flagellin antibodies that are suitable for determining anti-flagellin antibody levels include, e.g., a flagellin protein such as flagellin X, flagellin A, flagellin B, Cbir-1 flagellin, fragments thereof, and combinations thereof; a flagellin polypeptide having substantially the same amino acid sequence as the flagellin protein; a fragment thereof such as an immunoreactive fragment thereof; and combinations thereof.

In another embodiment, the methods of the present invention provide high clinical parameter (e.g., sensitivity, specificity, negative predictive value, positive predictive value, overall agreement) values for diagnosing the presence or severity of IBD. For example, in certain instances, the diagnosis of the presence or severity of IBD has a sensitivity of at least about 80% (e.g., at least about 85%, 90%, or 95%) and a specificity of at least about 90% (e.g., at least about 91%, 92%, 93%, 94%, or 95%).

In yet another embodiment, when an individual is diagnosed as having IBD, the methods of the present invention further comprise diagnosing the clinical subtype of IBD in the individual. In a preferred embodiment, the individual is diagnosed as having a clinical subtype of IBD selected from the group consisting of CD, UC, and IC.

In certain instances, the individual is diagnosed as having CD when:
 (a) the level of ASCA-IgA is above an ASCA-IgA cut-off value;
 (b) the level of ASCA-IgG is above an ASCA-IgG cut-off value;
 (c) the level of anti-OmpC antibody is above an anti-OmpC antibody cut-off value; or
 (d) the level of anti-I2 antibody is above an anti-I2 antibody cut-off value.

Preferably, the ASCA-IgA cut-off value, ASCA-IgG cut-off value, anti-OmpC antibody cut-off value, and anti-I2 antibody cut-off value are independently selected to achieve an optimized clinical parameter selected from the group consisting of sensitivity, specificity, negative predictive value, positive predictive value, overall agreement, and combinations thereof.

In certain other instances, the individual is diagnosed as having UC when the level of ANCA is above an ANCA cut-off value. Preferably, the ANCA cut-off value is selected to achieve an optimized clinical parameter selected from the group consisting of sensitivity, specificity, negative predictive value, positive predictive value, overall agreement, and combinations thereof.

In another embodiment, the diagnosis comprises calculating a second index value for the individual using an algorithm based upon the level of at least one IBD marker and diagnosing the individual as having CD, UC, or IC based upon the second index value.

In a preferred embodiment, the algorithm for calculating the second index value is a regression algorithm having the following formula:

$$\text{Index Value} = \text{Exp}(b_0 + b_1 * x_1 + \ldots + b_n * x_n)/(1 + \text{Exp}(b_0 + b_1 * x_1 + \ldots + b_n * x_n)),$$

wherein
 $b_1$ is an intercept value;
 $b_1$ is the regression coefficient of the first marker;
 $x_1$ is the concentration level of the first marker;
 $b_n$ is the regression coefficient of the $n^{th}$ marker;
 $x_n$ is the concentration level of the $n^{th}$ marker; and
 n is an integer of from 1 to 6.

In another aspect, the present invention provides a method for differentiating between CD, UC, and IC in an individual, the method comprising:
 (a) determining a level of at least one marker selected from the group consisting of ANCA, ASCA-IgA, ASCA-IgG, an anti-OmpC antibody, an anti-I2 antibody, and an anti-flagellin antibody in a sample from the individual;
 (b) calculating an index value for the individual using an algorithm based upon the level of at least one marker; and
 (c) diagnosing the individual as having CD, UC, or IC based upon the index value.

In certain instances, the method of the present invention for differentiating between CD, UC, and IC is performed on an individual previously diagnosed with IBD. In certain other instances, the method of the present invention for differentiating between CD, UC, and IC is performed on an individual not previously diagnosed with IBD.

In yet another aspect, the present invention provides a method for monitoring the efficacy of IBD therapy in an individual, the method comprising:
 (a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;
 (b) calculating an index value for the individual using an algorithm based upon the level of at least one marker; and
 (c) determining the presence or severity of IBD in the individual based upon the index value.

In one embodiment, the index value is compared to an index cutoff value. In another embodiment, the methods of the present invention further comprise comparing the index value from step (b) to the index value for the individual at an earlier time. In certain instances, a decrease in the index value from step (b) as compared to the index value calculated at an earlier time indicates an increase in the efficacy of IBD therapy. Alternatively, a decrease in the index value from step (b) as compared to the index value calculated at an earlier time indicates a decrease in the efficacy of IBD therapy. In certain other instances, an increase in the index value from step (b) as compared to the index value calculated at an earlier time indicates an increase in the efficacy of IBD therapy. Alternatively, an increase in the index value from step (b) as compared to the index value calculated at an earlier time indicates a decrease in the efficacy of IBD therapy. As used herein, a therapeutic agent useful in IBD therapy is any compound, drug, procedure, or regimen used to improve the health of the individual and includes any of the therapeutic agents described above.

Instill yet another aspect, the present invention provides a method for monitoring the progression or regression of IBD in an individual, the method comprising:
 (a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;
 (b) calculating an index value for the individual using an algorithm based upon the level of at least one marker; and
 (c) determining the presence or severity of IBD in the individual based upon the index value.

In one embodiment, the index value is compared to an index cutoff value. In another embodiment, the methods of the present invention further comprise comparing the index value from step (b) to the index value for the individual at an earlier time. In certain instances, the index value is used to predict the progression of IBD, e.g., by determining a likelihood for IBD to progress either rapidly or slowly in an individual based on the index value or based on a comparison of the index value to the index value calculated at an earlier time. In certain other instances, the index value is used to predict the regression of IBD, e.g., by determining a likelihood for IBD to regress either rapidly or slowly in an individual based on the index value or based on a comparison of the index value to the index value calculated at an earlier time. For example, a decrease in the index value from step (b) as compared to the index value calculated at an earlier time can indicate either a rapid or slow progression or regression of IBD. Alternatively, an increase in the index value from step (b) as compared to the index value calculated at an earlier time can indicate either a rapid or slow progression or regression of IBD.

In a further aspect, the present invention provides a method for optimizing therapy in an individual having IBD, the method comprising:

(a) determining a level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in a sample from the individual;

(b) calculating an index value for the individual using an algorithm based upon the level of at least one marker; and (c) determining a course of therapy in the individual based upon the index value.

In one embodiment, the index value is compared to an index cutoff value. In another embodiment, the methods of the present invention further comprise comparing the index value from step (b) to the index value for the individual at an earlier time. As such, a comparison of the two index values provides an indication for the need to change the course of therapy or an indication for the need to adjust the dose of the current course of therapy. In certain instances, a higher index value from step (b) indicates a need to change the course of therapy. In certain other instances, a higher index value from step (b) indicates a need to increase the dose of the current course of therapy. Alternatively, a higher index value from step (b) indicates a need to decrease the dose of the current course of therapy. One skilled in the art will know of suitable higher or lower doses to which the current course of therapy can be adjusted such that IBD therapy is optimized.

IV. IBD Markers

A variety of IBD markers, such as biochemical markers, serological markers, genetic markers, or other clinical or echographic characteristics, are suitable for use in the methods of the present invention. Examples of biochemical and serological markers include, without limitation, ANCA, ASCA-IgA, ASCA-IgG, anti-OmpC antibodies, anti-I2 antibodies, anti-flagellin antibodies, elastase, lactoferrin, calprotectin, and combinations thereof. An example of a genetic marker is the NOD2/CARD 15 gene. One skilled in the art will know of additional IBD markers suitable for use in the methods of the present invention.

The determination of ANCA levels in a sample is particularly useful in the methods of the present invention. For example, 60-80% of patients with UC have a perinuclear ANCA (pANCA) staining pattern that is found less frequently in CD and other disorders of the colon. Serum titers of ANCA are also elevated in patients with UC, regardless of clinical status. High levels of serum ANCA also persist in patients with UC five years post-colectomy. Although pANCA is found only very rarely in healthy adults and children, healthy relatives of patients with UC have an increased frequency of pANCA, indicating that pANCA may be an immunogenetic susceptibility marker. ANCA reactivity is also present in a small portion of patients with CD. The reported prevalence in CD varies, with most studies reporting that 10-30% of CD patients express ANCA (Saxon et al., *J. Allergy Clin. Immunol.*, 86:202-210 (1990); Cambridge et al., *Gut,* 33:668-674 (1992); Pool et al., *Gut,* 3446-50 (1993); Brokroelofs et al., *Dig. Dis. Sci.,* 39:545-549 (1994)).

ANCA is directed to cytoplasmic and/or nuclear components of neutrophils and encompass all varieties of anti-neutrophil reactivity, including, but not limited to, cANCA, pANCA, NSNA, and SAPPA. Preferably, ANCA levels in a sample from an individual are determined using an immunoassay such as an enzyme-linked immunosorbent assay (ELISA) with alcohol-fixed neutrophils. Other antigens specific for ANCA that are suitable for determining ANCA levels are described above.

The determination of ASCA-IgA and/or ASCA-IgG levels in a sample is also particularly useful in the methods of the present invention. Previous reports indicate that such antibodies can be elevated in patients having CD, although the nature of the *S. cerevisiae* antigen supporting the specific antibody response in CD is unknown (Sendid et al., *Clin. Diag. Lab. Immunol.,* 3:219-226 (1996)). ASCA may represent a response against yeast present in common food or drink or a response against yeast that colonize the gastrointestinal tract. Studies with periodate oxidation have shown that the epitopes recognized by ASCA in CD patient sera contain polysaccharides. Oligomannosidic epitopes are shared by a variety of organisms, including different yeast strains and genera, filamentous fungi, viruses, bacteria, and human glycoproteins. Thus, mannose-induced antibody responses in CD may represent a response against a pathogenic yeast organism or against a cross-reactive oligomannosidic epitope present, for example, on a human glycoprotein autoantigen. Regardless of the nature of the antigen, elevated levels of serum ASCA are believed to be a differential marker for CD, with only low levels of ASCA reported in UC patients (Sendid et al., supra, (1996)).

Anti-*Saccharomyces cerevisiae* antibodies such as ASCA-IgA and ASCA-IgG react specifically with antigens found in *S. cerevisiae*. Suitable antigens include any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA include, without limitation, whole killed yeast cells such as *Saccharomyces* cells (e.g., *S. cerevisiae, S. uvarum*) or *Candida* cells (e.g., *C. albicans*); yeast cell wall mannan such as phosphopeptidomannan (PPM); oligosaccharides such as oligomannosides; neoglycolipids; anti-ASCA idiotypic antibodies; etc.

Preparations of yeast cell wall mannans, e.g., PPM, can be used in determining the levels of ASCA-IgA and/or ASCA-IgG in a sample. Such water-soluble surface antigens can be prepared by any appropriate extraction techniques known in the art, including, for example, by autoclaving, or can be obtained commercially (see, Lindberg et al., *Gut*, 33:909-913 (1992)). The acid-stable fraction of PPM is also useful in the methods of the present invention (Sendid et al., supra, (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.,* 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man(1-2) Man. Such an oligomannoside can be purified from PPM as described in, e.g., Faille et al., supra, (1992). An exemplary neoglycolipid specific for ASCA can be constructed by releasing the oligomannoside from its respective PPM and subsequently coupling the released oligomannoside to 4-hexadecylaniline or the like.

The determination of anti-OmpC antibody levels in a sample is also particularly useful in the methods of the present invention. The outer membrane protein C (OmpC) belongs to the porin family of transmembrane proteins found in the outer membranes of bacteria, including gram-negative enteric bacteria such as *E. coli*. The porins provide channels for the passage of disaccharides, phosphates, and similar molecules. Porins can be trimers of identical subunits arranged to form a barrel-shaped structure with a pore at the center (Lodish et al., In "Molecular Cell Biology," Chapter 14 (1995)).

Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display. Regardless of the nature of the antigen, elevated levels of serum anti-OmpC antibodies are believed to be a differential marker for CD.

The determination of anti-I2 antibody levels in a sample is also particularly useful in the methods of the present invention. The microbial I2 protein is a polypeptide of 100 amino acids sharing some similarity to bacterial transcriptional regulators, with the greatest similarity in the amino-terminal 30 amino acids. For example, the I2 protein shares weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display. Regardless of the nature of the antigen, elevated levels of serum anti-I2 antibodies are believed to be a differential marker for CD.

The determination of anti-flagellin antibody levels in a sample is also particularly useful in the methods of the present invention. Microbial flagellins are proteins found in bacterial flagellum that arrange themselves in a hollow cylinder to form the filament. Suitable flagellin antigens useful in determining anti-flagellin antibody levels in a sample include, without limitation, a flagellin protein such as flagellin X, flagellin A, flagellin B, Cbir-1 flagellin, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display. Regardless of the nature of the antigen, elevated levels of serum anti-flagellin antibodies are believed to be a useful marker for diagnosing IBD and for differentiating between clinical subtypes of IBD.

V. Clinical Subtypes of IBD

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra, (1994)).

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

Indeterminate colitis (IC) is a clinical subtype of IBD that includes both features of CD and UC. Such an overlap in the symptoms of both diseases can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC.

VI. Assays

A variety of assays can be used to determine the levels of one or more IBD markers in a sample.

The methods of the present invention rely, in part, on detecting at least one IBD marker or determining the level of at least one IBD marker in a sample. As used herein, the term "detecting at least one marker" refers to determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining a level of at least one marker" refers to determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining a level of a marker is also useful for detecting the marker.

Flow cytometry can be used to determine the levels of one or more IBD markers in a sample. Such flow cytometric assays, including bead based immunoassays, can be used to determine, e.g., ANCA, ASCA-IgA, ASCA-IgG, anti-OmpC antibody, anti-I2 antibody, and/or anti-flagellin antibody levels in the same manner as described for detecting serum antibodies to *Candida albicans* and HIV proteins (see, e.g., Bishop and Davis, *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for an IBD marker can also be used to determine the levels of one or more IBD markers in a sample. Phage particles expressing an antigen specific for, e.g., ANCA, ASCA-IgA, ASCA-IgG, anti-OmpC antibody, anti-I2 antibody, and/or anti-flagellin antibody can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego: Academic Press, Inc. (1996)).

A variety of immunoassay techniques, including competitive and non-competitive immunoassays, can be used to determine the levels of one or more IBD markers in a sample (see, Self and Cook, *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL).

If desired, such immunoassays can be automated. Immunoassays can also be used in conjunction with laser induced fluorescence (see, e.g., Schmalzing and Nashabeh, *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the present invention (see, Rongen et al., *J. Immunol. Methods*, 204:105-133 (1997)).

Immunoassays are particularly useful for determining the levels of one or more IBD markers in a sample. A fixed neutrophil ELISA, for example, is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein or a fragment thereof is useful for determining whether a sample is positive for anti-flagellin antibodies, or for determining anti-flagellin antibody levels in a sample.

An enzyme such as horseradish peroxidase (HRP), alkaline phosphatase (AP), β-galactosidase, or urease can be linked to a secondary antibody selective for one of the IBD markers. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

Antigen capture assays can be useful in the methods of the present invention. For example, in an antigen capture assay, an antibody directed to an IBD marker is bound to a solid phase and sample is added such that the IBD marker is bound by the antibody. After unbound proteins are removed by washing, the amount of bound marker can be quantitated using, for example, a radioimmunoassay (Harlow and Lane, Antibodies: A Laboratory Manual, Cold Spring Harbor Laboratory, New York, 1988)). Sandwich enzyme immunoassays can also be useful in the methods of the present invention. For example, in a two-antibody sandwich assay, a first antibody is bound to a solid support, and the IBD marker is allowed to bind to the first antibody. The amount of the IBD marker is quantitated by measuring the amount of a second antibody that binds the IBD marker.

A radioimmunoassay using, for example, an iodine-125 ($^{125}$I) labeled secondary antibody (Harlow and Lane, "Antibodies: A Laboratory Manual," Cold Spring Harbor Laboratory: New York, (1988)) is also suitable for determining the levels of one or more IBD markers in a sample. A secondary antibody labeled with a chemiluminescent marker can also be useful in the methods of the present invention. A chemiluminescence assay using a chemiluminescent secondary antibody is suitable for sensitive, non-radioactive detection of IBD marker levels. Such secondary antibodies can be obtained commercially from various sources, e.g., Amersham Lifesciences, Inc. (Arlington Heights, Ill.).

In addition, a detectable reagent labeled with a fluorochrome is also suitable for determining the levels of one or more IBD markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. A particularly useful fluorochrome is fluorescein or rhodamine. Secondary antibodies linked to fluorochromes can be obtained commercially, e.g., goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked reagents, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the invention can be automated or performed robotically, and the signal from multiple samples can be detected simultaneously.

Immunoassays using a secondary antibody selective for an IBD marker are particularly useful for determining marker levels in a sample. As used herein, the term "antibody" refers to a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Liposome immunoassays, such as flow-injection liposome immunoassays and liposome immunosensors, are also suitable for use in the methods of the present invention (see, Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Quantitative western blotting also can be used to detect or determine the level of one or more IBD markers in a sample. Western blots can be quantitated by well known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the levels of one or more IBD markers in a sample. The term immunohistochemical assay encompasses techniques that utilize the visual detection of fluorescent dyes or enzymes coupled (i.e., conjugated) to antibodies that react with the IBD marker using fluorescent microscopy or light microscopy and includes, without limitation, direct fluorescent antibody, indirect fluorescent antibody (IFA), anticomplement immunofluorescence, avidin-biotin immunofluorescence, and immunoperoxidase assays. An IFA assay, for example, is useful for determining whether a sample is positive for ANCA, the level of ANCA in a sample, and/or an ANCA staining pattern (e.g., cANCA, pANCA, NSNA, and SAPPA). The concentration of ANCA in a sample can be quantitated, e.g., through endpoint titration or through measuring the visual intensity of fluorescence compared to a known reference standard.

In addition to the above-described assays for detecting or determining the levels of IBD markers, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Analysis of the genotype of a IBD marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260:1649-1652 (1993); Drmanac et al., *Nature Biotech.,* 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in an IBD marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Alternatively, the presence or level of an IBD marker can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of an IBD marker can also be determined by well-known methods including, without limitation, Bradford assays, Coomassie blue staining, silver staining, assays for radiolabeled protein, and mass spectrometry.

VII. Cut-Off Value Determination

In some embodiments, the present invention provides methods for differentiating between CD, UC, and IC in an individual diagnosed as having IBD. In certain instances, CD, UC, or IC is diagnosed when IBD markers such as ANCA, ASCA-IgA, ASCA-IgG, anti-OmpC antibodies, anti-I2 antibodies, and/or anti-flagellin antibodies are above cut-off values independently selected for each marker. In certain other instances, CD, UC, or IC is diagnosed when an algorithm based upon the level of IBD markers is used to determine an index value, and a comparison of the index value to an index cut-off value differentiates between CD, UC, and IC.

Cut-off values can be determined and independently adjusted for each of a number of IBD markers to observe the effects of the adjustments on clinical parameters such as sensitivity, specificity, negative predictive value, positive predictive value, and overall agreement. In particular, Design of Experiments (DOE) methodology can be used to simultaneously vary the cut-off values and to determine the effects on the resulting clinical parameters of sensitivity, specificity, negative predictive value, positive predictive value, and overall agreement. The DOE methodology is advantageous in that variables are tested in a nested array requiring fewer runs and cooperative interactions among the cut-off variables can be identified. Optimization software such as DOE Keep It Simple Statistically (KISS) can be obtained from Air Academy Associates (Colorado Springs, Colo.) and can be used to assign experimental runs and perform the simultaneous equation calculations. Using the DOE KISS program, an optimized set of cut-off values for a given clinical parameter and a given set of IBD markers can be calculated. ECHIP optimization software, available from ECHIP, Inc. (Hockessin, Del.), and Statgraphics optimization software, available from STSC, Inc. (Rockville, Md.), are also useful for determining cut-off values for a given set of IBD markers. Alternatively, cut-off values can be determined using Receiver Operating Characteristic (ROC) curves and adjusted to achieve the desired clinical parameter values.

As used herein, the term "sensitivity" refers to the probability that a diagnostic method of the present invention gives a positive result when the sample is positive, e.g., having IBD. Sensitivity is calculated as the number of true positive results divided by the sum of the true positives and false negatives. Sensitivity essentially is a measure of how well a method of the present invention correctly identifies those with IBD from those without the disease. The marker values can be selected such that the sensitivity of diagnosing IBD in an individual is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, or 95%. Preferably, the sensitivity of diagnosing IBD in an individual is about 80% at an index cutoff value of 0.62 (see, Example 4).

As used herein, the term "specificity" refers to the probability that a diagnostic method of the present invention gives a negative result when the sample is not positive, e.g., not having IBD. Specificity is calculated as the number of true negative results divided by the sum of the true negatives and false positives. Specificity essentially is a measure of how well a method of the present invention excludes those who do not have IBD from those who have the disease. The marker values can be selected such that the specificity of diagnosing IBD in an individual is at least about 70%, for example, at least about 75%, 80%, 85%, 90%, 91%, 92%, 93%, 94%, 95%, 96%, 97%, 98%, or 99%. Preferably, the specificity of diagnosing IBD in an individual is about 91% at an index cutoff value of 0.62 (see, Example 4).

As used herein, the term "negative predictive value" or "NPV" refers to the probability that an individual diagnosed as not having IBD actually does not have the disease. Negative predictive value can be calculated as the number of true negatives divided by the sum of the true negatives and false negatives. Negative predictive value is determined by the characteristics of the diagnostic method as well as the prevalence of the disease in the population analyzed. The marker cut-off values can be selected such that the negative predictive value in a population having a disease prevalence is in the range of about 80-99% and can be, for example, at least about 80%, 85%, 90%, 91%, 92%, 93%, 94%, 95%, 96%, 97%, 98%, or 99%.

The term "positive predictive value" or "PPV" refers to the probability that an individual diagnosed as having IBD actually has the disease. Positive predictive value can be calculated as the number of true positives divided by the sum of the true positives and false positives. Positive predictive value is determined by the characteristics of the diagnostic method as well as the prevalence of the disease in the population analyzed. The marker cut-off values can be selected such that the positive predictive value in a population having a disease prevalence is in the range of about 80-99% and can be, for example, at least about 80%, 85%, 90%, 91%, 92%, 93%, 94%, 95%, 96%, 97%, 98%, or 99%.

Predictive values, including negative and positive predictive values, are influenced by the prevalence of the disease in the population analyzed. In the methods of the present invention, the marker cut-off values can be selected to produce a desired clinical parameter for a clinical population with a particular IBD prevalence. For example, marker cut-off values can be selected for an IBD prevalence of up to about 1%, 2%, 3%, 4%, 5%, 6%, 7%, 8%, 9%, 10%, 15%, 20%, 25%, 30%, 35%, or 40%, which can be seen, e.g., in a clinician's office such as a gastroenterologist's office or a general practitioner's office.

As used herein, the term "overall agreement" or "overall accuracy" refers to the accuracy with which a method of the present invention diagnoses a disease state. Overall accuracy is calculated as the sum of the true positives and true negatives divided by the total number of sample results and is affected by the prevalence of the disease in the population analyzed. For example, the marker cut-off values can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, or 95%. Preferably, the overall accuracy of differentiating between CD and UC in an individual is about 80% at an index cutoff value of 0.39 (see, Example 5).

VIII. Examples

The following examples are offered to illustrate, but not to limit, the claimed invention.

Example 1

Determination of ANCA Levels

This example illustrates an analysis of ANCA levels in a sample using an ELISA assay.

A fixed neutrophil enzyme-linked immunosorbent assay (ELISA) was used to detect ANCA as described in Saxon et al., *J. Allergy Clin. Immunol.*, 86:202-210 (1990). Briefly, microtiter plates were coated with $2.5\times10^5$ neutrophils per well from peripheral human blood purified by Ficoll-hypaque centrifugation and treated with 100% methanol for 10 minutes to fix the cells. Cells were incubated with 0.25% bovine serum albumin (BSA) in phosphate-buffered saline to block nonspecific antibody binding for 60 minutes at room temperature in a humidified chamber. Next, control and coded sera were added at a 1:100 dilution to the bovine serum/phosphate-buffered saline blocking buffer and incubated for 60 minutes at room temperature in a humidified chamber. Alkaline phosphatase-conjugated goat $F(ab')_2$ anti-human immunoglobulin G antibody (γ-chain specific; Jackson Immunoresearch Labs, Inc.; West Grove, Pa.) was added at a 1:1000 dilution to label neutrophil-bound antibody and incubated for 60 minutes at room temperature. A solution of p-nitrophenol phosphate substrate was added, and color development was allowed to proceed until absorbance at 405 nm in the positive control wells was 0.8-1.0 optical density units greater than the absorbance in blank wells.

A panel of twenty verified negative control samples was used with a calibrator with a defined ELISA Unit (EU) value. The base positive/negative cut-off for each ELISA run was defined as the optical density (OD) of the Calibrator minus the mean (OD) value for the panel of twenty negatives (plus 2 standard deviations) times the EU value of the Calibrator. The base cut-off value for ANCA reactivity was therefore about 10 to 20 EU, with any patient sample having an average EU value greater than the base cut-off marked as ELISA positive for ANCA reactivity. Similarly, a patient sample having an average EU value is less than or equal to the base cut-off is determined to be negative for ANCA reactivity.

Example 2

Determination of ASCA Levels

This example illustrates the preparation of yeast cell well mannan and an analysis of ASCA levels in a sample using an ELISA assay.

Yeast cell wall mannan was prepared as described in Faille et al., *Eur. J. Clin. Microbiol. Infect. Dis.*, 11:438-446 (1992) and in Kocourek et al., *J. Bacteriol.*, 100:1175-1181 (1969). Briefly, a lyophilized pellet of yeast *Saccharomyces uvarum* was obtained from the American Type Culture Collection (#38926). Yeast were reconstituted in 10 ml 2×YT medium, prepared according to Sambrook et al., In "Molecular Cloning," Cold Spring Harbor Laboratory Press (1989). *S. uvarum* were grown for two to three days at 30° C. The terminal *S. uvarum* culture was inoculated on a 2×YT agar plate and subsequently grown for two to three days at 30° C. A single colony was used to inoculate 500 ml 2×YT media, and grown for two to three days at 30° C. Fermentation media (pH 4.5) was prepared by adding 20 g glucose, 2 g bacto-yeast extract, 0.25 g $MgSO_4$, and 2.0 ml 28% $H_3PO_4$ per liter of distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 g/l sodium citrate; pH 7.0±0.1) to each 100 g of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant was retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6-8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded, then the wash procedure was repeated until the supernatant was colorless, approximately two to three times. The precipitate was collected on a scintered glass funnel, washed with methanol, and air dried overnight. On some occasions, the precipitate was collected by centrifugation at 5000 rpm for 10 minutes before washing with methanol and air drying overnight. The dried mannan powder was dissolved in distilled water to a concentration of approximately 2 g/ml.

A *S. uvarum* mannan ELISA was used to detect ASCA. *S. uvarum* mannan ELISA plates were saturated with antigen as follows. Purified *S. uvarum* mannan prepared as described above was diluted to a concentration of 100 µg/ml with phosphate buffered saline/0.2% sodium azide. Using a multichannel pipettor, 100 µl of 100 µg/ml *S. uvarum* mannan was added per well of a Costar 96-well hi-binding plate (catalog no. 3590; Costar Corp., Cambridge, Mass.). The antigen was allowed to coat the plate at 4° C. for a minimum of 12 hours. Each lot of plates was compared to a previous lot before use. Plates were stored at 2-8° C. for up to one month.

Patient sera were analyzed in duplicate for ASCA-IgA or ASCA-IgG reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:80 for analysis of ASCA-IgA and 1:800 for analysis of ASCA-IgG and incubated for 1 hour at room temperature. Wells were washed three times with PBS/0.05% Tween-20. Then, a 1:1000 dilution of alkaline phosphatase-conjugated goat anti-human IgA (Jackson Immunoresearch; West Grove, Pa.) or a 1:1000 dilution of alkaline phosphatase-conjugated goat anti-human IgG F(ab')$_2$ (Pierce; Rockford, Ill.) was added, and the microtiter plates were incubated for 1 hour at room temperature. A solution of p-nitrophenol phosphate in diethanolamine substrate buffer was added, and color development was allowed to proceed for 10 minutes. Absorbance at 405 nm was analyzed using an automated EMAX plate reader (Molecular Devices; Sunnyvale, Calif.).

To determine the base cut-off value for ASCA-IgA and ASCA-IgG, single point calibrators having fixed EU values were used. OD values for patient samples were compared to the OD value for the calibrators and multiplied by the calibrator assigned values. The base cut-off value for ASCA-IgA ELISA was 20 EU. The base cut-off value for ASCA-IgG was 40 EU.

Example 3

Determination of Anti-I2 Antibody Levels

This example illustrates the preparation of recombinant I2 protein and an analysis of anti-I2 antibody levels in a sample using an ELISA assay or a histological assay.

The full-length I2-encoding nucleic acid sequence was cloned into the GST expression vector pGEX. After expression in *E. coli*, the protein was purified on a GST column. The purified protein was shown to be of the expected molecular weight by silver staining, and had anti-GST reactivity upon Western blot analysis.

ELISA analysis was performed with the GST-I2 fusion polypeptide using diluted patient or normal sera. Reactivity was determined after subtracting reactivity to GST alone. Varying dilutions of Crohn's disease (CD) sera and sera from normal individuals were assayed for IgG reactivity to the GST-I2 fusion polypeptide. Dilutions of 1:100 to 1:1000 resulted in significantly higher anti-I2 polypeptide reactivity for the CD sera as compared to normal sera. These results indicate that the I2 protein is differentially reactive with CD sera as compared to normal sera.

Human IgA and IgG antibodies that bind the GST-I2 fusion polypeptide were detected by direct ELISA assays essentially as follows. Plates (Immulon 3; DYNEX Technologies; Chantilly, Va.) were coated overnight at 4° C. with 100 µl/well GST-I2 fusion polypeptide (5 µg/ml in borate buffered saline, pH 8.5). After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of CD serum, ulcerative colitis (UC) serum, or normal control serum, diluted 1:100. The plates were then incubated for 2 hours at room temperature and washed as before. Alkaline phosphatase-conjugated secondary antibody (goat anti-human IgA (α-chain specific); Jackson ImmunoResearch; West Grove, Pa.) was added to the IgA plates at a dilution of 1:1000 in BSA-PBS. For IgG reactivity, alkaline phosphatase conjugated secondary antibody (goat anti-human IgG (γ-chain specific); Jackson ImmunoResearch) was added. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01 M Tris, pH 8.6, was added at 100 µl/well, and color allowed to develop for one hour. The plates were then analyzed at 405 nm. Using a cutoff that is two standard deviations above the mean value for the normal population, nine of ten CD values were positive, while none of the normal serum samples were positive. Furthermore, seven of ten CD patients showed an $OD_{405}$ greater than 0.3, while none of the UC or normal samples were positive by this measure. These results indicate that immunoreactivity to the I2 polypeptide, in particular, IgA immunoreactivity, can be used to diagnose CD.

For histological analysis, rabbit anti-I2 antibodies were prepared using purified GST-I2 fusion protein as the immunogen. GST-binding antibodies were removed by adherence to GST bound to an agarose support (Pierce; Rockford, Ill.), and the rabbit sera validated for anti-I2 immunoreactivity by ELISA analysis. Slides were prepared from paraffin-embedded biopsy specimens from CD, UC, and normal controls. Hematoxylin and eosin staining were performed, followed by incubation with I2-specific antiserum. Binding of antibodies was detected with peroxidase-labeled anti-rabbit secondary antibodies (Pierce; Rockford, Ill.). The assay was optimized to maximize the signal to background and the distinction between CD and control populations.

Example 4

Determination of Anti-OmpC Antibody Levels

This example illustrates the preparation of OmpC protein and an analysis of anti-OmpC antibody levels in a sample using an ELISA assay.

The following protocol describes the purification of OmpC protein using spheroplast lysis. OmpF/OmpA-mutant *E. coli* were inoculated from a glycerol stock into 10-20 ml of Luria Bertani broth supplemented with 100 μg/ml streptomycin (LB-Strep; Teknova; Half Moon Bay, Calif.) and cultured vigorously at 37° C. for about 8 hours to log phase, followed by expansion to 1 liter in LB-Strep over 15 hours at 25° C. The cells were harvested by centrifugation. If necessary, cells are washed twice with 100 ml of ice cold 20 mM Tris-Cl, pH 7.5. The cells were subsequently resuspended in ice cold spheroplast forming buffer (20 mM Tris-Cl, pH 7.5; 20% sucrose; 0.1M EDTA, pH 8.0; 1 mg/ml lysozyme), after which the resuspended cells were incubated on ice for about 1 hour with occasional mixing by inversion. If required, the spheroplasts were centrifuged and resuspended in a smaller volume of spheroplast forming buffer (SFB). The spheroplast pellet was optionally frozen prior to resuspension in order to improve lysis efficiency. Hypotonic buffer was avoided in order to avoid bursting the spheroplasts and releasing chromosomal DNA, which significantly decreases the efficiency of lysis.

The spheroplast preparation was diluted 14-fold into ice cold 10 mM Tris-Cl, pH 7.5 containing 1 mg/ml DNaseI and was vortexed vigorously. The preparation was sonicated on ice 4×30 seconds at 50% power at setting 4, with a pulse "On time" of 1 second, without foaming or overheating the sample. Cell debris was pelleted by centrifugation and the supernatant was removed and clarified by centrifugation a second time. The supernatant was removed without collecting any part of the pellet and placed into ultracentrifuge tubes. The tubes were filled to 1.5 mm from the top with 20 mM Tris-Cl, pH 7.5. The membrane preparation was pelleted by ultracentrifugation at 100,000×g for 1 hr at 4° C. in a Beckman SW 60 swing bucket rotor. The pellet was resuspended by homogenizing into 20 mM Tris-Cl, pH 7.5 using a 1 ml pipette tip and squirting the pellet closely before pipetting up and down for approximately 10 minutes per tube. The material was extracted for 1 hr in 20 mM Tris-Cl, pH 7.5 containing 1% SDS, with rotation at 37° C. The preparation was transferred to ultracentrifugation tubes and the membrane was pelleted at 100,000×g. The pellet was resuspended by homogenizing into 20 mM Tris-Cl, pH 7.5 as before. The membrane preparation was optionally left at 4° C. overnight.

OmpC was extracted for 1 hr with rotation at 37° C. in 20 mM Tris-Cl, pH 7.5 containing 3% SDS and 0.5 M NaCl. The material was transferred to ultracentrifugation tubes and the membrane was pelleted by centrifugation at 100,000×g. The supernatant containing extracted OmpC was then dialyzed against more than 10,000 volumes to eliminate high salt content. SDS was removed by detergent exchange against 0.2% Triton. Triton was removed by further dialysis against 50 mM Tris-Cl. Purified OmpC, which functions as a porin in its trimeric form, was analyzed by SDS-PAGE. Electrophoresis at room temperature resulted in a ladder of bands of about 100 kDa, 70 kDa, and 30 kDa. Heating for 10-15 minutes at 65-70° C. partially dissociated the complex and resulted in only dimers and monomers (i.e., bands of about 70 kDa and 30 kDa). Boiling for 5 minutes resulted in monomers of 38 kDa.

The OmpC direct ELISA assays were performed essentially as follows. Plates (USA Scientific; Ocala, Fla.) were coated overnight at 4° C. with 100 μl/well OmpC at 0.25 μg/ml in borate buffered saline, pH 8.5. After three washes in 0.05% Tween 20 in phosphate buffered saline (PBS), the plates were blocked with 150 μl/well of 0.5% bovine serum albumin in PBS, pH 7.4 (BSA-PBS) for 30 minutes at room temperature. The blocking solution was then replaced with 100 μl/well of Crohn's disease or normal control serum, diluted 1:100. The plates were then incubated for 2 hours at room temperature and washed as before. Alkaline phosphatase-conjugated goat anti-human IgA (α-chain specific), or IgG (γ-chain specific) (Jackson ImmunoResearch; West Grove, Pa.) was added to the plates at a dilution of 1:1000 in BSA-PBS. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM MgCl$_2$, 0.01M Tris, pH 8.6) was added at 100 μl/well, and color was allowed to develop for one hour. The plates were then analyzed at 405 nm. IgA OmpC positive reactivity was defined as reactivity greater than two standard deviations above the mean reactivity obtained with control (normal) sera analyzed at the same time as the test samples.

Example 5

Algorithm for Diagnosing IBD

This example illustrates an algorithm that was developed to diagnose IBD according to the methods of the present invention.

A retrospective analysis was conducted in a cohort of 402 patients using 275 IBD subjects, diagnosed by standard clinical practice. Controls included normal healthy volunteers (n=87) and non-IBD GI disease (n=40). The prevalence of IBD in the cohort=68%.

The levels of five IBD markers, ANCA, ASCA-IgA, ASCA-IgG, anti-OmpC, and pANCA were determined by an assay such as an immunoassay e.g., ELISA or IFA. These values were then subjected to regression analysis to derive the predictive algorithm (below) constructed from the concentration levels of the markers and their regression coefficients:

Index Value=$\text{Exp}(b_0+b_1*x_1+\ldots+b_5*x_5)/(1+\text{Exp}(b_0+b_1*x_1+\ldots+b_5*x_5))$, wherein
 $b_0$ is the intercept;
 $b_1$, $b_2$, $b_3$, $b_4$, and $b_5$ are the regression coefficients of ANCA, ASCA-IgA, ASCA-IgG, anti-OmpC, and pANCA respectively;
 $x_1$, $x_2$, $x_3$, $x_4$ and $x_5$ are the concentration levels of ANCA, ASCA-IgA, ASCA-IgG, anti-OmpC, and pANCA respectively;
 $b_1$ is −2.203790;
 $b_1$ is 1.208794 (ANCA);
 $b_2$ is 0.067421 (ASCA-IgA);
 $b_3$ is 0.022822 (ASCA-IgG);
 $b_4$ is 0.138847 (anti-OmpC); and
 $b_5$ is −0.839772 (PANCA IFA).

Based upon the above algorithm, an index cutoff value of 0.63 was determined. As such, a patient having an index value less than 0.63 is diagnosed as not having IBD, whereas a patient having an index value greater than 0.63 is diagnosed as having IBD. At this index cutoff value, the sensitivity for diagnosing IBD is 81.5% and the specificity is 92.1%.

FIG. 1 shows the diagnostic power of using an algorithmic approach based upon the levels of the above IBD markers. More particularly, FIG. 1 illustrates that the above algorithm using a combination of five IBD markers provided an area under the curve (AUC) of 0.908, which was substantially higher than the AUC obtained by relying on the level of only a single IBD marker, i.e., ANCA (AUC=0.762), ASCA-IgA (AUC=0.751), ASCA-IgG (AUC=0.697), and anti-OmpC (AUC=0.771). As such, the use of an algorithm based upon the levels of multiple markers for diagnosing IBD according to the methods of the present invention are advantageous over non-algorithmic techniques based upon the level of a single IBD marker.

Diagnosis of IBD

Table 1 shows the number of subjects and their test results.

TABLE 1

|  | CD | UC | Controls | Total |
|---|---|---|---|---|
| Test Positive | 145 | 79 | 10 | 234 |
| Test Negative | 30 | 21 | 117 | 168 |
|  | 175 | 100 | 127 | 402 |

As can be shown from Table 2, the likelihood ratio is greater using the methods of the present invention, compared to current technology. Further, this table shows improved clinical performance using the algorithms of the present invention

TABLE 2

|  | State of the art Test | Regression Algorithm of the Present Invention | |
|---|---|---|---|
| Prevalence |  | 68.4% |  | 95% CI |
| Sensititivity-IBD | 74.5% | 81.5% | 76.4-85.9% |
| CD | 76% | 82.9% | 76.4-88.1% |
| UC | 72.0% | 79.0% | 69.7-86.5% |
| Specificity | 91.3% | 92.1% | 86.0-96.2% |
| PPV | 94.9% | 95.7% | 92.2-97.9% |
| NPV | 62.4% | 69.6% | 62.1-76.4% |
| Accuracy | 79.9% | 84.8% | 62.1-76.4% |
| Likelihood Ratio | 8.6 | 10.3 | |

Example 6

Algorithm for Differentiating Between CD and UC

This example illustrates an algorithm that was developed to differentiate between CD, and UC according to the methods of the present invention.

The levels of three markers, ASCA-IgG, anti-OmpC, and pANCA, were determined by an assay such as an immunoassay (e.g., ELISA) for ASCA-IgG and anti-OmpC and by an indirect fluorescent antibody (IFA) assay for pANCA. These values were then subjected to regression analysis to derive the predictive algorithm (below) constructed from the concentration levels of the markers and their regression coefficients:

Index Value=$\text{Exp}(b_0+b_1*x_1+\ldots+b_3*x_3)/(1+\text{Exp}(b_0+b_1*x_1+\ldots+b_3*x_3))$, wherein
$b_0$ is the intercept;
$b_1$, $b_2$, and $b_3$ are the regression coefficients of ASCA-IgG, anti-OmpC, and pANCA, respectively;
$x_1$ and $x_2$ are the concentration levels of ASCA-IgG, anti-OmpC, and $x_3$ is the presence or absence of pANCA;
$b_0$ is 1.052567;
$b_1$ is −0.039619 (ASCA-IgG);
$b_2$ is −0.044386 (anti-OmpC); and
$b_3$ is 0.872890 (pANCA).

Based upon the above algorithm, an index cutoff value of 0.60 was determined. As such, a patient having an index value less than 0.60 is diagnosed as having CD and a patient having an index value greater than 0.60 is diagnosed as having UC. The area under the curve (AUC) was 0.875 and the algorithm had an overall accuracy of 85.7% for differentiating between CD and UC. As such, this example shows that the methods of the present invention for differentiating between clinical subtypes of IBD using an algorithm based upon the levels of multiple markers provide a high degree of overall accuracy for stratifying the disease into CD or UC. In instances where the methods of the present invention are used to differentiate between CD, UC, and IC, multivariate analysis can be used.

Differentiating CD and UC

TABLE 3

|  | CD (n = 145) | UC (n = 79) |
|---|---|---|
| % Correct | 88.3% | 81.0% |
| % Incorrect | 11.7% | 19.0% |
| Overall Accuracy | 85.7% (95% CI 80.4-90.0%) | |

|  | CD | UC |
|---|---|---|
| Control (n = 10) | 60% | 40% |

TABLE 4

|  | CD | UC | Controls | Total |
|---|---|---|---|---|
| Predicted CD | 128 | 15 ($^{11}/_{15}$ pANCA negative) | 6 | 149 |
| Predicted UC | 17 (all pANCA positive) | 64 | 4 (all pANCA positive) | 85 |
| Total | 145 | 79 | 10 | 234 |

Example 7

Algorithm for Diagnosing IBD or for Differentiating Between CD, UC, and IC

This example illustrates an additional algorithm that was developed to diagnose IBD or to differentiate between CD, UC, and IC according to the methods of the present invention. The description of using "stratified" values may also be applied to the other algorithms, for example prognosis.

The level of one or more IBD markers was determined by an assay such as an immunoassay (e.g., ELISA) or an indirect fluorescent antibody (IFA) assay. Each IBD marker was then assigned a value of 1, 2, or 3 based upon the level of the marker detected in a sample. Preferably, a value of 1, 2, or 3 is assigned based upon the cut-off value for the marker, such that a value of 1 indicates a level below the cut-off value, a value of 2 indicates a range around the cut-off, and a value of 3 indicates a range of values above level 2. For example, an ANCA level of less than about 10 EU is assigned a value of 1, an ANCA level of between about 10 and 20 EU is assigned a value of 2, and an ANCA level of greater than about 20 EU is assigned a value of 3. Similar assignments based upon the cut-off value can be performed for the level of any marker measured.

A cumulative index value was then determined by adding the individual values assigned for each marker. For example, a cumulative index value of 6 is calculated for a sample containing an ANCA level that has been assigned a value of 1, an ASCA-IgG level that has been assigned a value of 2, and an anti-OmpC level that has been assigned a value of 3. A diagnosis of IBD or a differentiation between CD, UC, and IC is then made based upon the cumulative index value. In one embodiment, the cumulative index value is compared to a cumulative index cut-off value. In certain instances, a patient having a cumulative index value greater than the cumulative index cut-off value is diagnosed as having IBD. In certain other instances, a patient having a cumulative index value greater than the cumulative index cut-off value is diagnosed as having either CD, UC, or IC.

Example 8

This Example Shows the Frequency Distribution of Positive Anti-Microbial Antibodies Related to Small Bowel Location, Surgery and Other Complications in CD For CD, trend analysis showed that there was a significant association between the absolute number of anti-microbial antibodies detected in the serum and the presence of small bowel location, surgery and number of surgeries, and complications such as fibrostenosis or fistula. Thus, using the methods of the present invention, it is possible to predict the prognosis of the disease, such as being able to predict the probable course and outcome of the disease and the likelihood of recovery. Table 5 shows the results.

TABLE 5

| | | # of positive antibodies | | | | |
|---|---|---|---|---|---|---|
| | | 0 | 1 | 2 | 3 | P value* |
| Small bowel CD | No | 32% | 29% | 21% | 18% | 0.0051 |
| N = 185 | Yes | 20% | 15% | 26% | 40% | |
| CD surgery | No | 32% | 19% | 19% | 30% | 0.0024 |
| N = 188 | Yes | 14% | 15% | 31% | 40% | |
| # CD surgeries | 0 | 32% | 19% | 19% | 25% | <0.0001 |
| N = 188 | 1 | 19% | 19% | 32% | 30% | |
| | 2 | 18% | 18% | 23% | 41% | |
| | ≧3 | 0% | 7% | 34% | 59% | |
| Complication | None | 37% | 12% | 21% | 30% | 0.0016 |
| N = 107 | fibrostenosis | 13% | 19% | 31% | 38% | |
| | fistula | 3% | 19% | 25% | 53% | |

*P values: Mantel-Haenszel chi-squared for trend

Thus, the foregoing results indicate that it is possible to predict the probable course and outcome of the disease using the methods of the present invention.

Example 9

This Example Shows Algorithms for Antimicrobial Antibodies Associated with Complications of CD Table 6 shows that logistic regression models incorporating different combinations of antimicrobial antibodies were associated with complications of IBD.

TABLE 6

Algorithms for complications in CD

| | Odds Ratio | 95% CI | AUC | p Value |
|---|---|---|---|---|
| Need for Surgery | | | | |
| I2, OmpC and ASCA A | 3.88 | 2.11-7.14 | 0.70 | <0.0001 |
| Fistulizing Disease | | | | |
| I2, OmpC and ASCA IgG | 7.56 | 2.69-21.20 | 0.81 | <0.0001 |
| Fibrostenosing Disease | | | | |
| OmpC and ASCA IgG | 3.51 | 1.31-9.37 | 0.74 | 0.01 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for optimizing therapy in an individual having inflammatory bowel disease (IBD) and receiving a course of therapy for the treatment of IBD, said method comprising:
    (a) obtaining a biological sample from said individual;
    (b) measuring a concentration level of at least one marker selected from the group consisting of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-I2 antibody, and an anti-flagellin antibody in said sample obtained from said individual;
    (c) applying a logistic regression algorithm to the measured concentration level of said at least one marker to calculate an index value for said individual;
    (d) comparing the index value calculated from step (c) to an index value for said individual that was calculated at an earlier time during said course of therapy; and
    (e) determining a subsequent dose of said course of therapy for said individual based upon said comparison from step (d), wherein a higher index value calculated from step (c) indicates a need to increase the subsequent dose of said course of therapy.

2. The method of claim 1, wherein said course of therapy is selected from the group consisting of an aminosalicylate, a corticosteroid, a thiopurine, methotrexate, infliximab, and a combination thereof.

3. The method of claim 1, wherein step (b) comprises measuring the concentration level of at least two of said markers.

4. The method of claim 1, wherein step (b) comprises measuring the concentration level of at least three of said markers.

5. The method of claim 1, wherein step (b) comprises measuring the concentration level of at least four of said markers.

6. The method of claim 1, wherein step (b) comprises measuring the concentration level of at least five of said markers.

7. The method of claim 1, wherein step (b) comprises measuring the concentration level of all six of said markers.

8. The method of claim 1, wherein step (b) comprises measuring the concentration level of ANCA, ASCA-IgA, ASCA-IgG, and anti-OmpC antibody.

9. The method of claim 1, wherein step (b) further comprises measuring a concentration level of at least one marker selected from the group consisting of elastase, lactoferrin, and calprotectin.

10. The method of claim 1, wherein said logistic regression algorithm has the following formula:

$$\text{Index Value}=\text{Exp}(b_0+b_1*x_1+\ldots+b_n*x_n)/(1+\text{Exp}(b_0+b_1*x_1+\ldots+b_n*x_n)),$$

wherein $b_0$ is an intercept value;
$b_1$ is the regression coefficient of the first marker;
$x_1$ is the concentration level of the first marker;
$b_n$ is the regression coefficient of the $n^{th}$ marker;
$x_n$ is the concentration level of the $n^{th}$ marker; and
n is an integer of from 1 to 6.

11. The method of claim 1, wherein the concentration level of said marker is measured by assaying said sample with an enzyme-linked immunosorbent assay (ELISA).

12. The method of claim 1, wherein the concentration level of ANCA is measured by assaying the binding between ANCA and fixed neutrophils.

13. The method of claim 1, wherein the concentration level of ASCA-IgA or ASCA-IgG is measured by assaying the binding between ASCA-IgA or ASCA-IgG and an antigen selected from the group consisting of yeast cell wall mannan, a purified oligomannoside antigen, a synthetic oligomannoside antigen, and combinations thereof.

14. The method of claim 13, wherein said antigen is yeast cell wall phosphopeptidomannan (PPM).

15. The method of claim 14, wherein said yeast cell wall PPM is *S. uvarum* PPM.

16. The method of claim 1, wherein the concentration level of anti-OmpC antibody is measured by assaying the binding between the anti-OmpC antibody and an OmpC protein or an immunoreactive fragment of said OmpC protein.

17. The method of claim 1, wherein the concentration level of anti-I2 antibody is measured by assaying the binding between the anti-I2 antibody and an I2 protein or an immunoreactive fragment of said I2 protein.

18. The method of claim 1, wherein the concentration level of anti-flagellin antibody is measured by assaying the binding between the anti-flagellin antibody and a flagellin protein or an immunoreactive fragment of said flagellin protein.

19. The method of claim 18, wherein said flagellin protein is selected from the group consisting of flagellin X, flagellin A, flagellin B, Cbir-1 flagellin, immunoreactive fragments thereof, and combinations thereof.

20. The method of claim 1, wherein said sample is a serum sample.

21. The method of claim 1, wherein said IBD is selected from the group consisting of Crohn's disease (CD), ulcerative colitis (UC), and indeterminate colitis (IC).

* * * * *